United States Patent [19]

Hogg

[11] 4,361,803
[45] Nov. 30, 1982

[54] APPARATUS FOR RECIRCULATING SWEEP FLOW ELECTROLYTE WITHOUT A PUMP

[75] Inventor: Walter R. Hogg, Miami, Fla.

[73] Assignee: Coulter Electronics, Inc., Hialeah, Fla.

[21] Appl. No.: 181,496

[22] Filed: Aug. 26, 1980

[51] Int. Cl.³ .................................... G01N 27/00
[52] U.S. Cl. ........................................ 324/71 CP
[58] Field of Search ............................ 324/71 CP

[56] References Cited

U.S. PATENT DOCUMENTS 3,746,976  7/1973  Hogg ........................ 324/71 CP
3,902,115  8/1975  Hogg ........................ 324/71 CP

*Primary Examiner*—Michael J. Tokar
*Attorney, Agent, or Firm*—Gerald R. Hibnick

[57] ABSTRACT

Disclosed is a particle analyzing apparatus including a first vessel of particulate electrolyte suspension, and an electrolyte-containing first chamber, and an electrolyte-containing second chamber, a sensing aperture formed in a wall between the vessel and the first chamber, a cleaning orifice formed in a wall between the first chamber and the second chamber, an electrical current passing through the sensing aperture to generate detectable signals with the passage of the particles through the sensing aperture, and a fluid recirculating system providing a fluid path from the second chamber through a filter for removing the particles to the first chamber, which is powered by waste kinetic energy of the suspension exiting from the sensing aperture.

11 Claims, 6 Drawing Figures

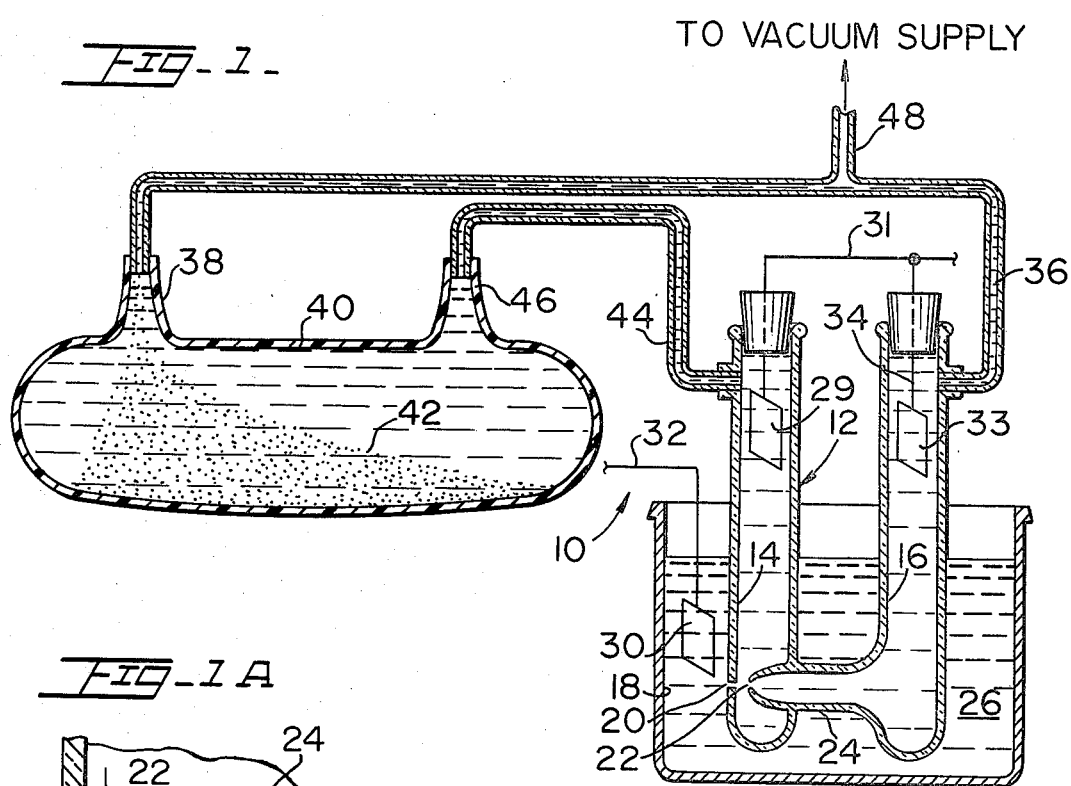
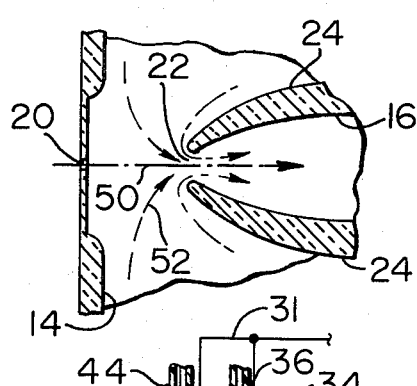
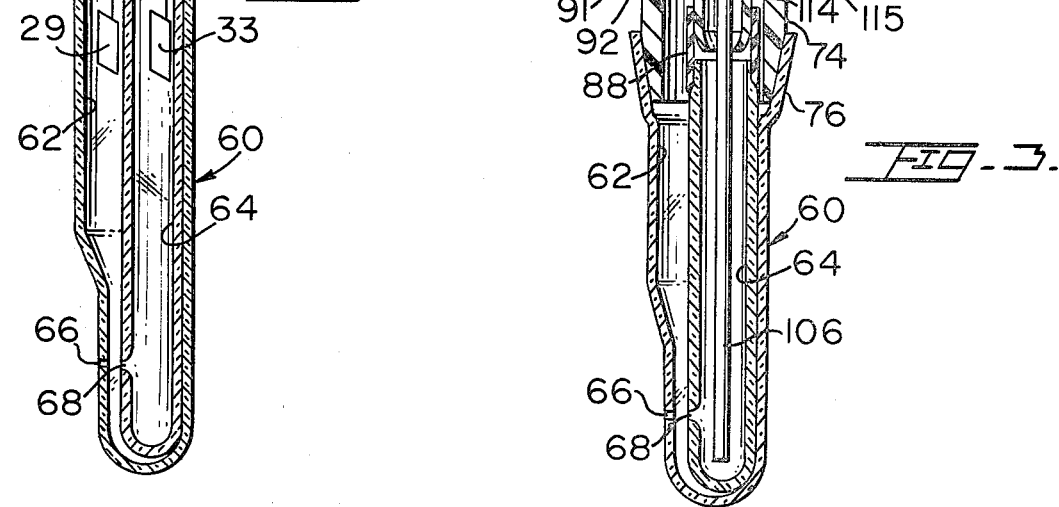

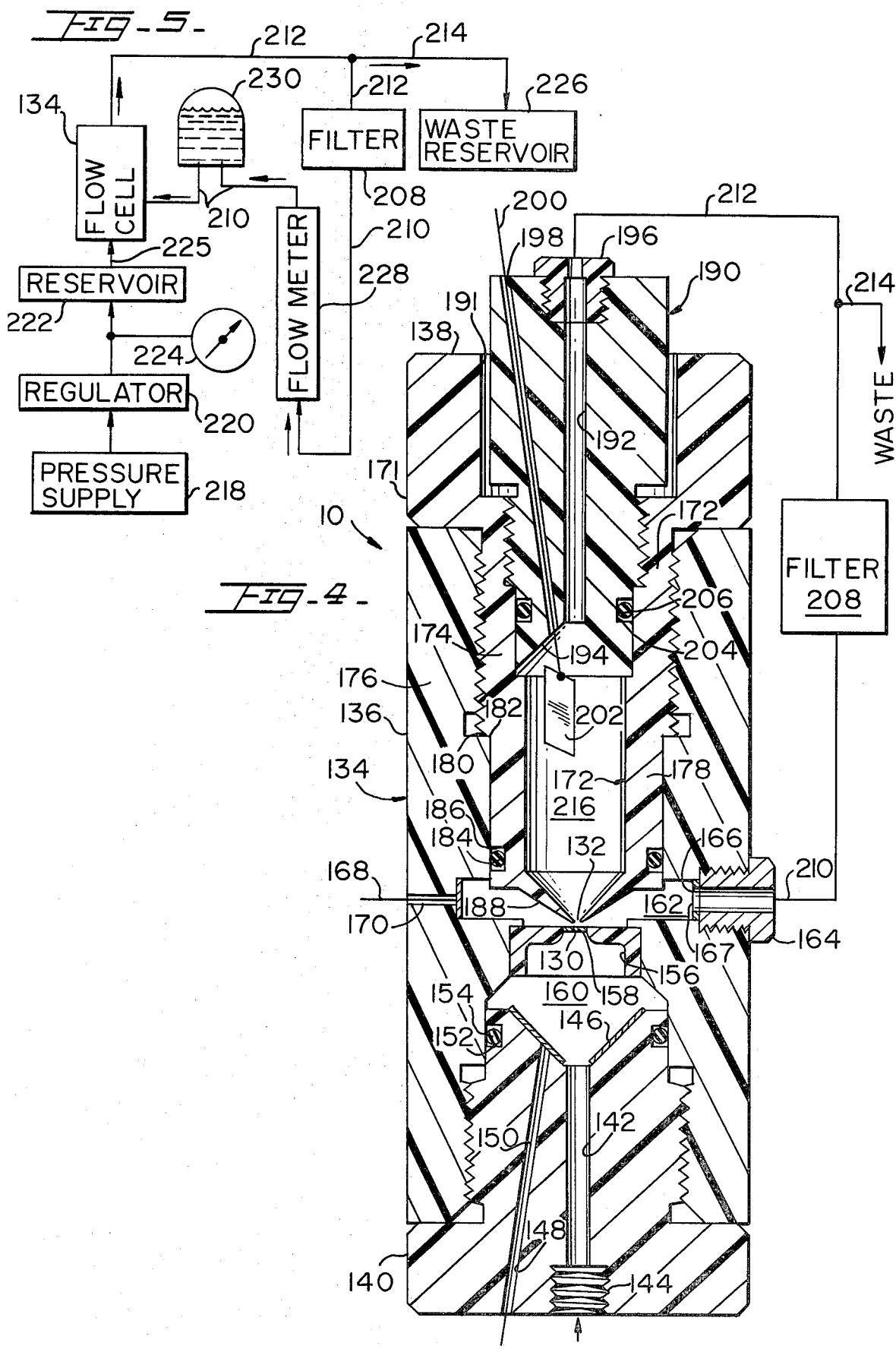

APPARATUS FOR RECIRCULATING SWEEP FLOW ELECTROLYTE WITHOUT A PUMP

BACKGROUND OF THE INVENTION

1. Field of the Invention

This invention relates generally to the art of studying the physical properties of particles carried in suspension and more particularly is concerned with improved apparatus for obtaining signals from particles passing through a scanning aperture without extraneous interference from other particles.

2. Description of the Prior Art

Particles of microscopic size and larger are counted and sized throughout the world by use of an apparatus known as the Coulter Counter ®. These apparatuses are constructed in accordance with the principles of U.S. Pat. No. 2,656,508 to Coulter, wherein there are a pair of vessels, which are formed of insulating material and have a minute aperture between them. A suspension of the particles to be studied flows from one vessel to the other through the aperture. An electrical current is established through the aperture by use of suitable electrodes suspended in the respective bodies of electrolyte liquid in the vessels and an electrical power source is connected across the electrodes. The displacement of fluid within the sensing zone of the apparatus, which zone includes the aperture, by the presence of a particle therein will cause a change in the impedance of the sensing zone, and this change is detected by suitable detecting means connected to the electrodes.

An apparatus disclosed in U.S. Pat. No. 3,299,354 to Hogg substantially decreases the possibility of undesirable spurious particle reading and count signals which sometimes occured in prior art devices, such as that disclosed in U.S. Pat. No. 2,656,508. This is accomplished by replacing the so-called aperture tube of prior art structures with a pair of chambers having an interconnection for separating the electrical and mechanical effects produced by particles passing through the aperture. Particles passing through the aperture of the apparatus immediately are transported away from the proximity of the aperture so that there is little or no chance of spurious signals resulting from said particles.

One of the objects of the invention disclosed in U.S. Pat. No. 3,299,354 was to provide an aperture tube which was self-cleaning in that the suspension in the immediate vicinity of the aperture was kept free of extraneous particles. However, eddy currents of fluid in the aperture tube on the downstream side of the aperture could occur and these eddy currents swirled into the sensing zone of the aperture. It was believed that the fluid downstream of the aperture would be stagnant liquid substantially devoid of particles, hence not introducing appreciable extraneous signals. While this was largely true, the action has been determined not to be sufficient to satisfy the more critical demands of today's technology. A small percentage of particles was not caught by the orifice in the elongate neck of the second chamber and these sometimes produced extraneous signals by virture of the eddy currents at the bottom of the first chamber of the aperture tube.

For purposes of resolving the aforesaid problems with regards to extraneous signals, the invention disclosed in U.S. Pat. No. 3,746,976 to Hogg and U.S. Pat. No. Re. 28,558 to Hogg provides a self-cleaning aperture tube with the addition of a pump device interposed between the first and second chambers to produce a closed system in which there are no inlets or outlets other than the aperture in the first chamber and a waste outlet. The pump operates to draw the particle suspension up through the second chamber and force the same back into the first chamber, completing a circuit around this path and creating a sheath flow in the first chamber to hydrodynamically focus the particles as they proceed toward an orifice into the second chamber. The flow created by the pump is such as to ensure that all particles introduced into the aperture tube are passed through, i.e. caught by the orifice of the second chamber so as to prevent the occurrence of extraneous signals.

The invention of U.S. Pat. No. 3,746,976 satisfactorily eliminates the extraneous signal problems inherent in the apparatus of U.S. Pat. No. 3,299,354. In so doing, however, the structure incorporates a pump and filter through which electrolyte is recirculated to achieve the cleaning flow. Further, the structure of U.S. Pat. No. 3,746,976 includes a relatively fragile and cumbersome aperture tube in which the chambers thereof are separated along a substantial portion of the tube.

The apparatus disclosed in U.S. Pat. No. 3,902,115 to Hogg, et al. provides an improved self-cleaning aperture tube. The aperture tube eliminates the above described disadvantages of the tube disclosed in U.S. Pat. No. 3,746,976 in which one chamber has a branch of lateral diversion which passes out of a second chamber and returns again. Further, the apparatus provides a system to supply fresh clean electrolyte from a reservoir and eliminates the need for recirculating the electrolyte through a pump and filter as in the structure of U.S. Pat. No. 3,746,976.

The apparatus of U.S. Pat. No. 3,902,115 uses an elaborate, non-circulating reservoir system, which requires the wasteful use of large quantities of electrolyte for the liquid sheath.

The above mentioned patents, U.S. Pat. Nos. 2,656,508; 3,299,354; 3,746,976; U.S. Pat. Nos. Re. 28,558; and 3,902,115 are incorporated herein as a part hereof by specific reference to the extent that incorporation may be needed for a better appreciation of the invention herein.

SUMMARY OF THE INVENTION

The invention is directed toward a particle analyzing apparatus for detecting the physical properties of particles. The apparatus includes a vessel of particulate liquid suspension, a first chamber containing a body of liquid, and a second chamber containing a body of liquid. An aperture holder forms a wall between the vessel and the first chamber, and has a sensing aperture form therein to provide a constricted liquid passageway between the vessel and the first chamber. An orifice holder forms a wall between the first chamber and the second chamber and has a cleaning orifice formed therein for providing a liquid passageway between the first chamber and the second chamber. An electrical current through the sensing aperture generates detectable electrical signals with the passage of the particles through the sensing aperture.

The improvement of the invention comprises providing "self-powered" sweep flow and filtration in a recirculating system, so as to eliminate spurious signals created by particles being whirled in eddy currents that pass through the sensing zone of the sensing aperture. Means are provided for fluidly coupling the second chamber through a filter means to the first chamber. The filter means includes at least a settling chamber for allowing the particles to settle out or a filter having relatively low fluid resistance or some combination thereof. In operation, a pressure drop is created across the sensing aperture, which causes the liquid suspension to jet into the first chamber. Energy is transferred from the jetting liquid suspension to the liquid in the first chamber so as to create a liquid sheath flow around the liquid suspension. This liquid sheath hydrodynamically focuses the liquid suspension, preventing particles from escaping into the first chamber and thereby preventing spurious signals. At the same time, a pressure rise created by the formation of the sheath flow causes liquid from the second chamber to flow through the filter means, wherein particles are removed. Particle free liquid from the filter means flows to the first chamber and provides the liquid for maintaining the liquid sheath flow. Hence, this arrangement eliminates the disadvantageous swirling effect of eddy currents, without the use of a pump as required by U.S. Pat. No. 3,746,976 or without requiring the use of a non-circulating reservoir system as shown in U.S. Pat. No. 3,902,115.

BRIEF DESCRIPTION OF THE DRAWINGS

Further objects and advantages of the present invention will become apparent as the following description proceeds, taken in conjunction with the accompanying drawing in which:

FIG. 1 is a cross-sectional view of the first embodiment of the particle analyzing apparatus embodying the invention, FIG. 1A is an enlarged fragmentary, cross-sectional view of the sensing aperture and cleaning orifice of FIG. 1, FIG. 2 shows an alternative aperture tube design implemented in the recirculating system of FIG. 1, FIG. 3 is a cross-sectional view of a second embodiment of the particle analyzing apparatus wherein the aperture tube of FIG. 2 is implemented into an alternative design for the recirculating system, FIG. 4 is a cross-sectional view of a third embodiment of the particle analyzing apparatus, and FIG. 5 is a schematic of the hydraulic system for providing the fluid flows to the embodiment of FIG. 4 and for optionally measuring fluid flows.

DESCRIPTION OF THE PREFERRED EMBODIMENTS

The apparatuses with which the structure according to the invention is intended for use is known as the Coulter® and Coulter Counter® particle analyzing devices. The Coulter® devices and principle of operation are referred to with particularity in the above cited patents; hence, the disclosure thereof will not be repeated except in instances where understanding of the invention will be enhanced. The marks "Coulter" and "Coulter Counter" are the Registered Trademarks, Registration Nos. 995,825 and 679,591, of Coulter Electronics, Inc., of Hialeah, Fla.

Referring to FIG. 1, a first embodiment of the invention is illustrated and is depicted as a modification of the particle analyzing apparatus disclosed in cited U.S. Pat. No. 3,746,976. In this embodiment, the particle analyzing apparatus, generally referred to by numeral 10, includes a multiple chamber aperture tube or vessel 12. The aperture tube 12, which includes a first chamber 14 and a second chamber 16, is suspended within a beaker or vessel 18. A sensing aperture 20 is formed in the wall of the first chamber 14 near the lower end thereof and a cleaning orifice 22 is formed in the wall of a neck portion 24 of the second chamber 16. The sensing aperture 20 and the cleaning orifice 22 are coaxially aligned. The vessel 18 retains a body of sample suspension 26 to be drawn through the aperture 20 and the orifice 22. A pair of electrodes 29 and 30 are positioned within the first chamber 14 and the vessel 18, respectively, and are connected to a detector (not shown) through leads 31 and 32, respectively, for the purpose of performing an analysis on the sample suspension. An electrode 33 is positioned in the second chamber 16 and is electrically coupled to the lead 31 by a lead 34. The electrode 29 can be omitted if the orifice 22 is large enough to preclude the generation of any secondary impedance pulses in the orifice 22. The electrode 29 otherwise is the principal impedance electrode, while electrode 33 mainly is useful in grounding any electrical noise picked up by fluid lines 36, 48 and 44, and other components which tend to act as "antennas." The fluid line 36 connects the second chamber 16 with an inlet fitting 38 of a settling chamber 40. The settling chamber 40 provides filter means for removing particles 42 which are denser than the electrolyte carrier fluid. A fluid line 44 connects an outlet fitting 46 to the first chamber 14. Preferably, the inlet and outlet fittings 38 and 46 have an interior surface with a cross section comprising an exponential curve to minimize turbulence and subsequent stirring. This assists the particles in settling through gravity to the bottom of the settling chamber 40 before the liquid exits from the outlet fitting 46. The fluid line 36 is in communication with a vacuum supply (not shown) through a fluid line 48. Conveniently, but not necessarily, the vessel 18 is maintained at atmospheric pressure and the second chamber 16 is held at a negative pressure relative to the pressure of the vessel 18. The second chamber 16 and the settling chamber 40 are held at the same pressure by the vacuum supply, except for small pressure drops to be described presently.

An enlargement of the sensing aperture 20 and the cleaning orifice 22 is shown in FIG. 1A to illustrate better the operation of the apparatus 10. The sample suspension 26 in the vessel 18 flows through the sensing aperture 20 in a relatively high velocity liquid jet, the velocity being a function of the pressure drop across the sensing aperture 20. This liquid jet, created by the suction of the vacuum supply, proceeds along a trajectory illustrated by an arrow 50. As is well known, when the streamlines of the suspension sample approach the fluid contraction of the sensing aperture 20, they assume a curved path and the total stream continues to neck down for some distance beyond the contraction, defining an area of small diameter flow called the vena contracta. In this region the cross section of the stream has a minimum flow area. As the sample suspension jets through the first chamber 14, the surrounding electrolyte in the immediate vicinity is carried along with it. The electrolyte from the first chamber 14 rushes in to replace that which is swept away and thereby forms a liquid sheath or sweep flow around the sample suspension. This sheath hydrodynamically focuses the sample suspension so that it passes through the cleaning orifice 22, without any of the sample suspension escaping into the first chamber 14. The formation of the liquid sheath in the first chamber 14 results in a pressure rise. This pressure differential, which exists in an equilibrium condition, circulates liquid, including the sample suspension, through the second chamber 16 into the settling chamber 40 by way of the fluid line 36. Due to the large volume of the settling chamber, the fluid therein is almost quiescent and therefore the particles, which are typically denser than the electrolyte, descend to the bottom of the settling chamber 40. The fluid flow, created by the pressure differential generated by the kinetic energy of the sample suspension, proceeds through the fluid line 44 back into the first chamber 14 to provide liquid for the continued development of the sheath flow around the sample suspension. In FIG. 1A, the sheath flow about the cleaning orifice 22 is illustrated by streamlines 52.

It has been found that the spacing between the sensing aperture 20 and the cleaning orifice 22 can vary substantially and still achieve a good sweep flow, but if the spacing is too small or too great, poor results are produced. Moreover, it has been found to be desirable to have the cleaning orifice 22 with a substantially larger diameter than the sensing aperture 20. A few illustrative dimensional combinations will be described below, but it should be understood that these values can vary substantially with no or minimal decreasing in the apparatus' ability to sweep away particles. It has been found experimentally that when the sensing aperture 20 has a 50 micrometer diameter, the spacing between the sensing aperture and the cleaning orifice 22 can be 0.077 inches and the diameter of the cleaning orifice 22 can be 0.009 inches. When the sensing aperture has a 70 micrometer diameter, the spacing can be 0.113 inches and the diameter of the cleaning orifice 22 can be 0.013 inches. When the sensing aperture 20 has a 100 micrometer diameter, the spacing can be 0.151 inches and the diameter of the cleaning orifice 22 can be 0.017 inches. As can be inferred from this data, for a given sized sensing aperture 20, the larger the diameter of the cleaning orifice 22, the further away the cleaning orifice 22 should be positioned with respect to the sensing aperture 20 so as to produce the maximum sweep flow. The greater the sweep flow, the greater the pressure rise across the cleaning orifice 22 or vice versa. For example, with the vacuum supply providing 21 inches of mercury as the total available vacuum, it has been found that a 0.2 inches of mercury pressure differential can be developed between the chambers 14 and 16 for recirculating the electrolyte.

With the pressure differential created by the sweep flow, as previously described, a recirculating flow will be developed from the second chamber 16 through the settling chamber 40 back to the first chamber 14. Since the particles settle out in the settling chamber 40, clean electrolyte is provided therefrom to the first chamber 14 and therefore prevents particles from straying into the sensing zone of the sensing aperture 20. Consequently, the sheath flow pulled through the cleaning orifice 22 not only provides the hydrodynamic forces for preventing the particles from being retained in the first chamber 14, but it also provides the pressure differential to create a fluid flow for moving the particles to the filter chamber 40 for gravitational settling, thereby generating a source of clean electrolyte for the first chamber 14. Hence, this arrangement eliminates the disadvantageous swirling effect of eddy currents, without the use of a pump as required by U.S. Pat. No. 3,746,976 or without requiring the wasteful use of a non-circulating, pressurized reservoir system as shown in U.S. Pat. No. 3,902,115.

FIG. 2 shows an interchangeable alternative form for the aperture tube 12 shown in FIG. 1, and is referred to by numeral 60. The aperture tube 60 is of similar design to that of U.S. Pat. No. 3,902,115. In the same manner as illustrated in FIG. 1, the aperture tube 60 is immersed in the sample suspension of the vessel 18 and has the same closed-loop circulatory system. The aperture tube 60 has a dual chamber arrangement which includes a first chamber 62 positioned in surrounding relationship to a second chamber 64. A sensing aperture 66 is formed in the wall of the first chamber 62 near the lower end thereof and a cleaning orifice 68 is formed in the wall of the second chamber 64 and is aligned in coaxial relationship with the sensing aperture 66. The fluid line 36 is in communication with the second chamber 64 in that it passes through a pair of bungs 69 and 70. The fluid line 44 passes through bung 69 to be in fluid communication with the first chamber 62. The aperture tube 60 is shown adapted to the recirculation system of FIG. 1 only for the purposes of illustrating that the aperture tubes in this arrangement can take many different forms, as shown by the variety of designs found in the cited patents. The preferred implementation of the aperture tube 60 is shown in FIG. 3, where the closed-loop circulatory system and filter differs in structure, but not in the general concept.

FIG. 3 shows a closed-loop recirculating and filtering arrangement, generally referred to by numerial 71, mounted on top of the aperture tube 60, which previously was illustrated in FIG. 2. The arrangement 71 includes a cylindrical housing 72, preferably formed of plastic, which has a lower flange 74 dimensioned and configured to matingly engage in sealed relationship with the correspondingly dimensioned rim 76 of the aperture tube 60. Preferably, the aperture tube 60 is formed of a clear material, such as glass to allow for optical viewing of the sensing aperture 66. The housing 72 has an upper, threaded portion 78 arranged to rotatably engage a threaded portion 80 of a plastic cap 82. An O-ring 84 is disposed in a cutout formed in the housing 72 and provides a sealing relationship between the cap 82 and the housing 72. A more or less centrally disposed tube 86 is mounted in fluid-tight relationship to the top of the second chamber 64 by means of a cylindrical, rubber gasket 88. A filter 90 is mounted interior to the housing 72 by a support base 91. The support base 91 has a plurality of radially aligned grooves 92 formed therein. The filter 90, which has a circular cross-sectional configuration, preferably comprises a corrugated, multi-fold fibrous filter. However, those skilled in the art will appreciate that numerous commercially available, porous filters can be adapted for use in the embodiment of FIG. 3. A circular plastic disc 93 is positioned above the filter 90. The disc 93 has a plurality of radially aligned grooves 94 formed therein. A pair of plastic caps 95 and 96 surround the filter 90 to maintain it in its cylindrical configuration. Mounted on top of the disc 93 is a rubber, circular end-seal and tube mount 98, which is wedged between the cap 82 and the disc 93 and protrudes outward to support a quick-refill tube 100. The upper portion of the cap 82 defines a fitting 102 to receive a fluid line or pipe 104. A waste withdrawal tube 106 passes through holes formed in the tube mount 98 and the disc 93 and extends down through the tube 86, with its lower extremity being positioned in the lower regions of the second chamber 64 substantially below the cleaning orifice 68. The filter 90 serves to remove particles from the sweep flow. Preferably, but not necessarily, the chamber 108 interior to the filter 90 allows the particles to settle onto the cap 96, thereby providing a longer life for the filter 90. In other words, the filter 90 can be used with a very small chamber 108 which merely allows the liquid to flow to the filter 90. However, to extend the life of the filter 90 and to reduce the frequency of cleaning the same, the chamber 108 is sized to define a settling chamber to allow at least some of the particles to settle out, thereby at least reducing the rate at which the filter 90 is clogged. A return flow chamber 110 is defined interior to the inner wall of the housing 72. The return flow chamber 110, at its lower end, fluidly connects with the grooves 92 and, at its upper end, fluidly connects with the grooves 94. The inwardly facing walls of the disc 93 and the cap 95 define a receiving chamber 112, which provides a fluid connection between the tube 100 and the grooves 94. The return flow chamber 110 is in fluid communication with the receiving chamber 112 through the plurality of grooves 94. The electrode 29 is positioned in the return flow chamber 110. A connecting chamber 114, which is interior to the flange 74, opens at its lower end into the first chamber 62 and is fluidly connected at its upper end to the return flow chamber 110 by the grooves 92. With the exception of the electrode 29 and its electrical connections, the components of the arrangement 71 are made of electrically non-conductive materials. A plastic washer 115 is positioned between the support base 91 and the housing 72. A rubber seal and tube mount 117 is positioned under the cap 95 in the interior confines of the filter 90.

In operation, the quick-refill tube 100 supplies clean electrolyte to the first chamber 62. The electrolyte proceeds down the tube 100 into the receiving chamber 112, through the grooves 94 into the return flow chamber 110, through the grooves 92 into the connecting chamber 114 so as to fill up the first chamber 62. This arrangement maintains pristine electrolyte in the first chamber 62. The sample suspension from the vessel 18 (not shown FIG. 3) jets through the sensing aperture 66, due to the fluid line 104 and/or the quick-refill tube 100 being coupled to a vacuum supply (not shown). In the same manner as previously described in the embodiment of FIG. 1, a sheath flow is developed around the jet of sample suspension in the first chamber 62, which in turn creates a pressure differential. This pressure differential causes the sample suspension containing the particles to flow up the second chamber 64 and into the chamber 108. The large size of the chamber 108 and the use of an expanding rim 122 of the tube 86 assist in providing a minimum of turbulence in the chamber 108 by having a minimum of acceleration and deceleration of the electrolyte. In this manner particles 124, generally adjacent the inner surface of the filter 90, settle from the electrolyte onto the cap 96, and thereby extends the life of the filter 90. Clean electrolyte then proceeds from the filter 90, while the particles are retained in the chamber 108. The clean electrolyte is then recirculated by proceeding into the first chamber 62, so as to provide sheath liquid for continuing the development of the sheath flow. The waste withdrawal tube 106 is positioned near the bottom of the second chamber 64 to avoid adding velocity to the sample suspension over and above that provided by the recirculating sweep flow. The cap 82 is removable through unscrewing, so as to allow the entire assembly to come apart, so that the filter 90 to be cleaned or changed, as desired.

To remove bubbles, it has been found desirable to have a stopcock coupled to the fluid line 104 and the quick-refill tube 100, so that the vacuum supply can be applied to one only and then to the other only, and thereby jar loose bubbles. While the sample suspension is being sucked through the sensing aperture 66, an equal amount of liquid will be proceeding toward the vacuum supply and will be collected in a waste reservoir (not shown). The amount of liquid circulating in the closed-loop recirculation system heretofore describe will be equal to the amount of liquid drawn by the sample suspension through the cleaning orifice 68 in the form of the liquid sheath. Although both of the embodiments of FIGS. 1 and 3 are shown with a vacuum supply for creating a pressure drop across the sensing aperture 66, it will be clear to those skilled in the art that it is the relative pressure differences that accomplish the flow. For instance, instead of having the vessel 18 at atmospheric pressure, the fluid line 48 could be maintained at atmospheric pressure and a positive pressure with respect thereto could be applied to the vessel 18. In the same manner previously described, an amount of liquid, equal to the sample suspension jetting through the sensing aperture, would be ejected from the fluid line 48.

A third embodiment of the apparatus 10 is illustrated in FIG. 4 and is particularly adapted for empirically determining the proper spacing between a sensing aperture 130 and a cleaning orifice 132 of a flow cell 134. The flow cell 134 comprises a main housing member 136 and a pair of end members 138 and 140, each of which are screwed into one of the ends of the main housing member 136. The end member 140 has a sample introduction bore 142 formed therein, which terminates into a threaded bore 144 for receiving the end of a fluid line (not shown). The opposed side of the end member 140 has a conic-shaped surface with an electrode 146 secured thereto. A fine drill hole 148 provides access for an electrical lead 150 to connect to the electrode 146. A cutout 152 is formed in the end of the end member 140 to retain an O-ring 154. An aperture holder 156 is secured to the main housing member 136 and acts to position axially an aperture wafer 158 containing the sensing aperture 130. The cavity formed between the aperture holder 156 and the electrode 146, along with its associated upstream conduits and reservoir (not shown), define a first vessel 160. A first chamber 162 is formed in the main housing member 136, with the downstream side of the sensing aperture 130 opening therein. A threaded fitting 164, for mounting a fluid conduit, is screwed into one side of the housing member 136 so as to be in fluid communication with the first chamber 162. A cylindrical electrode 166 is mounted about the periphery of the first chamber 162, with the exception of hole 167 for a fluid connection with the fitting 164. The electrode 166 is electrically connected to a lead 168, which passes through a drill hole 170 formed in the main housing member 136.

The end member 138 has an enlarged portion 171 and an elongated neck portion 172 extending therefrom. The neck portion 172 has a threaded part 174 dimensioned and configured to screw into threaded portion 176 of the main housing member 136. Extending from the threaded part 174 is a smooth cylindrical part 178. A stop ledge 180 is formed to abut against a ledge 182 formed at the junction of the threaded part 174 and the cylindrical part 178. When these two elements are in abutting relation, the cylindrical part 178 is extended to its maximum degree into the main housing member 136. An O-ring 184 is positioned in a cutout 186. A cone-shaped wall 188 is formed at the end of the cylindrical part 178 and has the cleaning orifice 132 central formed therein. The outwardly extending upstream side of the cone-shape wall 188 provides one of the surfaces defining the first chamber 162.

A core member 190 is rotatably screwed in secured relationship into a center cavity 191 of the end member 138. The core member 190 has an exit bore 192 axially formed therein. The bore 192 terminates at one end in a truncated cone-shape surface 194 and terminates at the upper end with a threaded fitting 196. A drill hole 198 allows access for an electrical lead 200 to connect with an electrode 202. A cutout 204, formed in the core member 190, retains an O-ring 206. The electrical leads 150, 168 and 200, corresponding to 32, 31 and 34 of FIG. 1, are connected to a detector in a conventional manner. As will be described in more detail hereinafter, a filter 208 is interposed in a closed-loop flow system by fluid lines or conduits 210 and 212. The filter 208 corresponds to 42 and 90 of the earlier two embodiments. A fluid conduit 214 connects the conduit 212 to a waste reservoir (not shown). As with all the embodiments, a sufficient pressure drop can be created across the sensing aperture 130 by applying a positive pressure upstream of the aperture 130 or a vacuum downstream of the aperture 130, for instance by attaching a vacuum supply to the conduit 214.

As described and presented up to this point, the basis operation of this third embodiment is the same as the two previously described embodiments of FIGS. 1 and 3. It is only the specific structure of the flow cells that differs, but the basic functions are the same. However, by rotating the end member 138, the spacing between the sensing aperture 130 and the cleaning orifice 132 can be adjusted to determine the optimum spacing for obtaining the maximum sheath flow through the cleaning orifice 132. By achieving the maximum sheath flow therethrough, the pressure differential for recirculation is also maximized. In so doing, excellent particle removal from the first chamber 162 is accomplished. The cavity, formed downstream of the cleaning orifice 132 interior to the neck portion 172, and its associated fluid lines and downstream reservoirs comprise a second chamber 216.

The hydrodynamic system for supplying the fluid flows of the embodiment of FIG. 4 is shown in more detail in FIG. 5. A variable source of pressure 218 is in communication through a pressure regulator 220 with a fluid reservoir 222 for the sample suspension. A pressure guage 224 monitors the pressure therein. The reservoir 222 is coupled by a conduit 225 to the sample introduction bore 142 (shown in FIG. 4) of the flow cell 134. The conduit 212 is in fluid communication with the filter 208 and, through the conduit 214, with a waste reservoir 226. The filter 208 is fluidly connected by the conduit 210 through a flow meter 228 and a bubble trap 230 to the first chamber 162 (shown in FIG. 4) of the flow cell 134. The interposing of the flow meter 228 into the fluid flow between the filter 208 and the flow cell 134 allows for the monitoring of the closed loop circulation, so as to determine when the maximum sheath flow is occurring. When the maximum or near maximum sheath flow has occurred, the good sweep flow results of removing particle from the first chamber 162 are achieved. The bubble trap 230 is preferably included for the removal of bubbles. Additionally, in that the flow call 134 can be readily disassembled, both the cleaning orifice 132 and the sensing aperture 130 can be changed so as to provide apertures 20 and orifices 22 with different diameters and lengths.

Although particular embodiments of the invention have been shown and described here, there is no intention to thereby limit the invention to the details of such embodiments. On the contrary, the intention is to cover all modification, alternatives, embodiments, usages and equivalents of the subject invention as fall within the spirit and scope of the invention, specification and the appended claims.

What is claimed is:

1. A particle analyzing apparatus including a vessel for holding sample liquid suspension of particles to be analyzed, a first chamber for containing a body of liquid, an aperture containing means forming a wall between said vessel and said first chamber, said aperture containing means having a sensing aperture provided therein to form a constricted liquid passageway between said vessel and said first chamber, a second chamber for containing a body of liquid, an orifice containing means forming a wall between said first chamber and said second chamber, said orifice containing means having a cleaning orifice provided therein to form a liquid passageway between said first chamber and said second chamber, means for providing an electrical current through said sensing aperture to generate detectable electrical signals with the passage of the particles through said sensing aperture, fluid moving means for providing a pressure difference across said sensing aperture to move a quantity of said liquid suspension from said vessel to said first chamber; means for providing a particle free liquid to said first chamber to form a liquid sheath around a quantity of said liquid suspension from said sensing aperture, the improvement comprising:
   said means for providing a particle free liquid to said first chamber comprising fluid conducting means for fluidly coupling said first chamber to said second chamber to provide a fluid recirculating loop;
   said fluid conducting means including a filter means for removing particles;
   said sensing aperture and cleaning orifice being spaced apart by a predetermined distance which is dependent upon at least one of the sizes of said sensing aperture and said cleaning orifice;
whereby said liquid suspension jets through said sensing aperture and forms said liquid sheath and a pressure differential, which circulates liquid from said second chamber through said filter means to said first chamber to provide said particle free liquid to said first chamber for continuous development of said liquid sheath.

2. The particle analyzing apparatus according to claim 1, wherein said filter means includes only a settling chamber for removing the particles.

3. The particle analyzing apparatus according to claim 2, wherein said settling chamber includes an inlet fitting and an outlet fitting, each said fitting including a fluid passageway having a decreasing diameter with respect to displacement from the interior of said settling chamber, said fluid conducting means further including a first fluid conduit connecting said inlet fitting to said second chamber and a second fluid conduit connecting said outlet fitting to said first chamber.

4. The particle analyzing apparatus according to claim 1, wherein said filter means includes only a filter composed of a liquid conducting, particle retaining material.

5. The particle analyzing apparatus according to claim 1, wherein said filter means includes a filter composed of a liquid conducting, particle retaining material, the apparatus further including a settling chamber positioned adjacent said filter in fluid communication therewith.

6. The particle analyzing apparatus according to claim 5, wherein said settling chamber is formed interior to said filter.

7. The particle analyzing apparatus according to claim 1, further including,
   means for adjusting said predetermined distance between said sensing aperture and said cleaning aperture.

8. The particle analyzing apparatus according to claim 7, further including,
   means for measuring the flow in said fluid conducting means to monitor the quantity of said liquid sheath.

9. The particle analyzing apparatus according to claim 1, wherein said predetermined distance between said sensing aperture and said cleaning orifice is dependent upon the diameters of both said sensing aperture and said cleaning orifice.

10. For use in a particle analyzing apparatus of the Coulter type in which a particle sensing aperture provides the only fluid and electrical current paths between two bodies of liquid and into a first chamber, a sample suspension being caused to flow through said sensing aperture and into said first chamber; said apparatus also including a cleaning orifice opening from said first chamber into a second chamber for receiving the flow of sample; particle free liquid being supplied into said first chamber for sheathing said flowing sample as it passes into said cleaning orifice; the improvement comprising,
   fluid conducting means coupling said first and second chambers in a circulatory loop for moving the particle free sheath liquid back into said first chamber from said second chamber;
   particle filter means lying within said fluid conducting means for filtering out the particles prior to the reentry of the sheathing liquid into said first chamber; the primary, if not exclusive, driving force for moving the sheath liquid in said circulatory loop and thus providing continuous development of particle free sheath liquid to the sample flow between said aperture and said orifice being the flow of sample suspension into said first chamber;
   said aperture and said orifice being separated by a distance which can optimize the flow of sheathed sample into said second chamber, said distance being a function of at least one of sample flow rate, aperture diameter, and orifice diameter.

11. The particle analyzing apparatus according to claim 1, wherein said sensing orifice has a diameter which is substantially smaller than the diameter of said cleaning orifice.

* * * * *